(12) United States Patent
Hetzel et al.

(10) Patent No.: US 8,105,616 B2
(45) Date of Patent: Jan. 31, 2012

(54) SKIN-PAMPERING CREAM LOTION

(75) Inventors: Frank Hetzel, Welle (DE); Rainer Kroepke, Schenefeld (DE); Jens Schulz, Schenefeld (DE); Stephanie von der Fecht, Wedel (DE)

(73) Assignee: Beiersdorf AG, Hamburg (DE)

( * ) Notice: Subject to any disclaimer, the term of this patent is extended or adjusted under 35 U.S.C. 154(b) by 1151 days.

(21) Appl. No.: 11/347,127

(22) Filed: Feb. 3, 2006

(65) Prior Publication Data

US 2006/0193806 A1 Aug. 31, 2006

(30) Foreign Application Priority Data

Feb. 4, 2005 (DE) .................. 20 2005 002 183 U

(51) Int. Cl.
*A61K 8/02* (2006.01)
(52) U.S. Cl. ........................................ 424/401; 514/939
(58) Field of Classification Search .................. 424/401; 514/939
See application file for complete search history.

(56) References Cited

U.S. PATENT DOCUMENTS

| | | | | |
|---|---|---|---|---|
| 3,424,849 A | * | 1/1969 | Judge, Jr. et al. | ............. 514/785 |
| 5,066,485 A | * | 11/1991 | Brieva et al. | .................... 424/63 |
| 5,250,289 A | * | 10/1993 | Boothroyd et al. | ............. 424/59 |
| 5,788,972 A | * | 8/1998 | De Salvert et al. | ............ 424/401 |
| 5,897,857 A | * | 4/1999 | Hillebrand et al. | ............ 424/703 |
| 2003/0017973 A1 | * | 1/2003 | Rodelet | ............................... 514/8 |
| 2004/0089195 A1 | * | 5/2004 | Moodycliffe et al. | ............ 106/3 |
| 2004/0123775 A1 | * | 7/2004 | Ono et al. | ................ 106/163.01 |

FOREIGN PATENT DOCUMENTS

| | | |
|---|---|---|
| WO | WO 2004/091477 A2 | 10/2004 |
| WO | WO 2004/103290 A2 | 12/2004 |
| WO | WO 2004/105703 A2 | 12/2004 |
| WO | WO 2005/000248 A2 | 1/2005 |
| WO | WO 2005/009385 A2 | 2/2005 |

OTHER PUBLICATIONS

Material Safety Data Sheet, Mineral Oil.*
Material Safety Data Sheet, Mineral Oil, created 1997, revised 2007.*

* cited by examiner

*Primary Examiner* — Brandon Fetterolf
*Assistant Examiner* — Paul Zarek
(74) *Attorney, Agent, or Firm* — Greenblum & Bernstein, P.L.C.

(57) ABSTRACT

A cosmetic preparation of the oil-in-water type whose oil phase comprises one or more mineral oils and which has a flow curve depicting the dynamic viscosity as a function of the shear stress showing a maximum of up to 10 000 Pas at a shear stress of from 5 to 50 Pa and a shoulder at a shear stress of from 30 to 110 Pa.

26 Claims, 1 Drawing Sheet

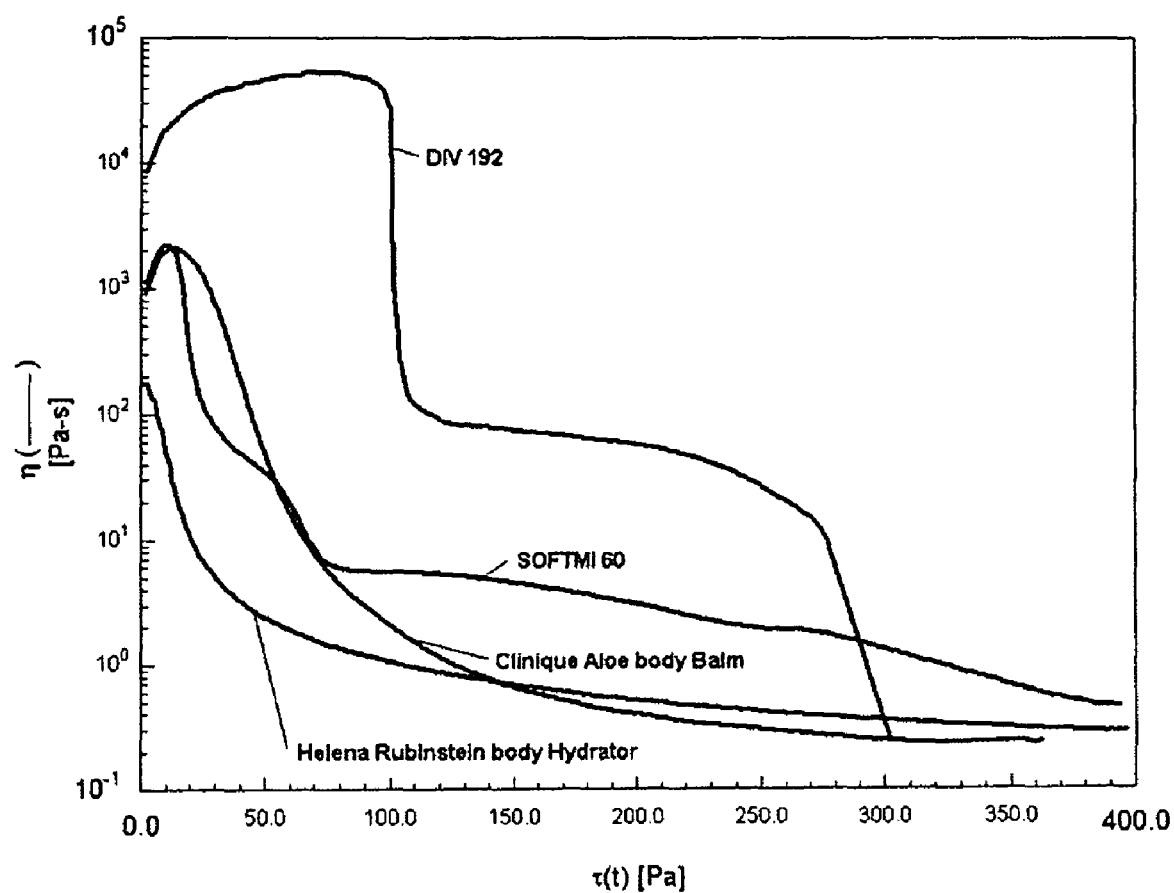

SKIN-PAMPERING CREAM LOTION

FIELD OF THE INVENTION

The present invention relates to cosmetic preparations—in particular cosmetic preparations of the oil-in-water type—with a particular creamy-soft texture.

BACKGROUND OF THE INVENTION

Cosmetics can comprehend all measures which, for aesthetic reasons, bring out changes on skin and hair or are used for washing the body. Cosmetics thus means to care for, to improve and to beautify the outside of the body in order, through vision, touch and smell, to please those around us and also ourselves. Even thousands of years ago, cosmetics were used by people for this purpose. Colour was applied to lips and face, valuable oils were used for anointing and scented water was used for bathing.

Whereas the cleaning effect of a shampoo, the improvement in combability of a hair rinse or the curling of the hair as a result of a perm can be established easily and objectively, other effects and properties of cosmetic products are virtually immeasurable or are only very noticeable to the individual. These include, for example, a certain (invigorating, soft, supple, smooth etc.) feel on the skin or the softness and suppleness of the skin following the application of a cosmetic, and the fullness and bounce of the hair and the like. In addition, the consumer's expectation is also governed by secondary properties of the product. These are, in particular, the scent and the colour of the cosmetic, and also its packaging, the price, the manufacturer and the advertising.

One property of cosmetic products which is very important for the consumer but which can only be quantitatively measured with difficulty is its texture. The term "texture" is understood as meaning those properties of a cosmetic which relate to the structure of the preparation, are perceived by the sense of touch and in some cases can be expressed in mechanical or rheological flow properties. The texture can, in particular, be tested by means of sensorics. The texture of cosmetic products, which can, if appropriate, be influenced using additives, is of virtually equal importance to the consumer as their effects which can be established objectively.

The term "sensorics" refers to the scientific discipline which deals with evaluating cosmetic preparations on the basis of sensory impressions. A sensory assessment of a cosmetic is made by reference to visual, olfactory and haptic impressions.

Visual impressions: all features which can be perceived by the eye (colour, shape, structure).

Olfactory impressions: all odour impressions which can be perceived by drawing in air through the nose, which can often be differentiated into initial odour (top note), main odour (middle note, body) and after-odour (finale). The volatile substances which are only released upon application also contribute to the olfactory impression.

Haptic impressions: all sensations of the sense of touch, which relate primarily to structure and consistency of the product.

Sensory analysis makes use of the possibility of integrally acquiring the overall sensory impression of a product. Disadvantages of sensory analysis are the subjectivity of the impression, the fact that the test persons can easily be influenced and the considerable scattering of results caused by this. These drawbacks are nowadays countered by using groups of trained test persons, screening the testers from one another, and statistical evaluation of the in most cases numerous analysis data.

The method of sensory analysis used most often in research and development is the difference test. The task here is usually restricted to recognizing one of several samples or sample differing from a control sample. Whereas with difference tests within one test only two samples are compared with one another, with the ranking test a series of three or more samples is to be determined, usually according to intensity, quality, popularity or similarity to a comparison sample. This (simple) method is suitable, for example, for a pre-selection of samples in product optimization and is also often used in market research.

Alternatively, the texture of a cosmetic preparation can also be characterized by reference to its rheological properties.

The term "viscosity" is understood as meaning the property of a liquid to offer resistance (tenacity, internal friction) to the mutual laminar displacement of two adjacent layers. This so-called dynamic viscosity according to $\eta=\tau/D$ is defined as the ratio of the shear stress to the rate gradient perpendicular to the direction of flow.

Whereas a graphical representation of the flow behaviour of Newtonian liquids at constant temperature produces a straight line, in the case of so-called non-Newtonian liquids, considerable deviations are often evident, depending on the particular shear stress $\tau$. In these cases, the so-called apparent viscosity can be determined which, whilst not obeying the Newtonian equation, can, however, be used to ascertain the true viscosity values through graphical methods.

The term yield point is understood as meaning the smallest shear stress above which a plastic material behaves in rheological terms like a liquid (DIN 1342-1: 1983-10). The yield point is determined by plotting a flow curve (DIN 53019: 1980-05; DIN 53214: 1982-02). The value obtained depends greatly on the time scale (strain rate) on which the measurement is based. The flow curve is a graphic representation of the relationship between shear stress and rate gradient D for a liquid subjected to lamellar flow or for a plastic material above the yield point. Flow curves are usually measured in rotary viscometers. In the case of speed-controlled systems, while presetting a continuously or step-wise varied rate gradient, the resulting torque is measured and the shear stress proportional to this is calculated. In the case of shear stress-controlled systems, the reverse is true. From the flow curve it is possible to calculate the viscosity as a function of the rate gradient, to determine yield points and to characterize the flow behaviour.

Cosmetic O/W formulations always have pseudoplastic flow behaviour with greater or lesser marked thixotropy which makes it easier for the consumer to apply such products. Furthermore, the extent and nature of the pseudoplasticity and also the thixotropy also determine the distribution on the skin and the feel of the skin after rubbing in because, for example, a thixotropic O/W formulation can, after spreading, again build up a (feelable) structure on the skin.

The person skilled in the art is of course aware of a large number of options for formulating stable O/W preparations for cosmetic or dermatological application, for example in the form of creams and ointments which are spreadable in the range from room temperature to skin temperature, or as lotions and milks, which are more flowable within this temperature range.

O/W emulsions for (large-area) application within the bodycare sector—i.e. O/W emulsions which, in particular, are to be removed from customary plastic bottles in a relatively large amount—are usually formulated so that they can be spread easily on the skin and at the same time allow good emptying of the last bits from the packaging. In order to be able to satisfy both criteria, the O/W emulsions of the prior art must accordingly have a rather low viscosity of at most 6000 mPa·s (determinable using a Haake viscotester VT-02 at 25° C.). This requirement placed on a corresponding skincare product leads accordingly always to identical or similar formulations.

SUMMARY OF THE INVENTION

It was an object of the present invention to find preparations which, besides the criteria customary for cosmetics, such as compatibility, storage stability and the like, also offer considerable, previously unknown cosmetic results for the consumer. In particular, the sought-after preparations should be suitable for use in the bodycare sector, i.e. for application to the entire body (and thus, distinct from a purely facial care application, in a relatively large amount). This means they should in particular be very easy to spread on the skin, should absorb rapidly and nevertheless be very rich and caring.

Surprisingly, it has been found that a cosmetic preparation, characterized in that its flow curve—in the form of a depiction of the dynamic viscosity as a function of the shear stress—has in the range from 5 to 50 Pa a maximum of up to 10 000 Pa·s and also in the further course of the flow curve at a shear stress of from 30 to 110 Pa a shoulder, is able to achieve these objects.

The flow curves of the preparations according to the invention are drawn using an SR-2000 from Rheometric Scientific (now TA-Instruments). This instrument is a shear-stress-controlled rheometer with an air-bearing transducer. The measurement system consists of a parallel plate measurement system (so-called plate/plate arrangement) with a diameter of 25 mm, where the lower plate can be heated using a Peltier couple. The measurement is carried out at a measuring temperature of 25° C. The measurement method chosen is a linear shear stress-time slope with a strain rate of 40 Pa/min starting at 0 Pa.

The preparations according to the invention are extremely satisfactory preparations in every respect. It was unforeseeable to the person skilled in the art that emulsions which, through targeted adjustment of the pseudoplastic flow behaviour (structural viscosity) and of the thixotropy, exhibit the properties according to the invention, despite a relatively high yield point, can be distributed in particular very easily on the skin, absorb rapidly and nevertheless are very rich and caring. The properties according to the invention impart to the preparation itself a creamy-soft texture ("good-feel texture") and are at the same time responsible for a velvety soft feel on the skin following application of the preparation: the skin feels pleasantly soft and supple, and this effect can last for the entire day.

The preparations according to the invention therefore represent a considerable enrichment of the prior art with regard to flowable preparations.

The preparations according to the invention are particularly preferably O/W emulsions.

BRIEF DESCRIPTION OF THE DRAWING

FIG. 1 is a graph showing the flow curves for preparation SOFTMI 60 according to the invention, DIV 192 from the comparative examples, and for two commercial products "Clinique Aloe Body Balm" and "Helena Rubinstein Body Hydrator".

DETAILED DESCRIPTION OF THE PREFERRED EMBODIMENTS

The texture according to the invention is obtainable, for example, if the oil phase of the preparations according to the invention comprises one or more of the following constituents with the constraints described in each case, or even consists entirely of these constituents:

Mineral Oils:

In a preferred embodiment with which the texture according to the invention can be realized particularly well, the oil phase comprises one or more mineral oils, in particular one or more paraffin oils. Paraffin oils (white oils) is the term used to refer to mixtures of purified, saturated aliphatic hydrocarbons (paraffins). The German Pharmacopoeia 10 describes, for example, two so-called medicinal white oils: thick-liquid ("higher-viscosity") paraffin oil (paraffinum liquidum) with a density of from 0.827 to 0.890 and a viscosity of from 110 to 230 mPa·s and thin-liquid ("low-viscosity") paraffin oil (paraffinum perliquidum) with a density of from 0.810 to 0.875 and a viscosity of from 25 to 80 mPa·s.

The texture according to the invention is obtainable particularly if the totality of the mineral oils—i.e. a mixture of all the mineral oils used—has the following properties:

a refractive index (at 20° C.) of from 1.475 to 1.480,
a kinematic viscosity (at 40° C.) of from 35 to 65 mm$^2$/s, in particular 40 to 55 mm$^2$/s and
a density (at 20° C.) of from 0.870 to 0.880.

The refractive index can be determined using the digital automatic Abbe refractometer ABBEMAT TYPE HP or TYPE WR (manufacturer: Dr Kernchen GmbH, Seelze). During this measurement, the critical angle is determined at which the total reflection of a beam of light passing from the optically more dense medium to the optically thinner medium occurs. The measurement range of the abovementioned refractometer is between 1.32 and 1.56 in the case of type HP and between 1.30 and 1.72 in the case of type WR, the measurement accuracy being 0.00001.

The kinematic viscosity can be determined using a capillary viscometer in accordance with Ubbelohde (viscometer AVS 440 with AVS/S from Schott Instruments GmbH, Mainz). The measurement principle is based on the dependency of the flow rate of a sample through a capillary on its viscosity. The time is measured in which a certain volume at a given pressure gradient flows through a capillary of a certain length and a certain radius. Here, the capillary has to be chosen so that the uncertainty attached to the Hagenbach-Couette correction does not exceed the error permitted for the time measurement. The kinematic viscosity v in mm$^2$/s is determined according to the following equation:

$$v = K * t$$

where K is an instrument constant which depends on the viscometer and the capillary chosen and t is the through-flow time.

The measurements are carried out in accordance with the DIN determinations DIN 1342, 51550, 51562 and 53012, and the determinations of the German Pharmacopoeia DAB V.6.7.1.

The density can be determined using the density measuring instrument PAAR DMA 48 (manufacturer: Anton Paar GmbH, Graz). The measurement method is based on the flexural resonator principle. The flexural resonator is an oscillating, U-shaped tube made of glass or metal. The sample to be analysed is poured into the U tube and the resonance frequency is determined. The resonance frequency depends on the mass of the tube together with sample. Since the volume and mass of the tube are known, it is possible to determine the density of the sample from the measured frequency.

It is of course possible and also advantageous for the purposes of the present invention to use only one mineral oil with the specified properties. However, for the purposes of the present invention, preference is also given to mixtures of two or more mineral oils provided the mixture of these mineral oils has the abovementioned properties.

Of particular advantage for realizing the texture according to the invention is also a mixture of paraffinum liquidum (for example with a refractive index (at 20° C.) of from 1.478 to 1.482 and a kinematic viscosity (at 40° C.) of from 65 to 72, and a density (at 20° C.) of from 0.873 to 0.885) and paraffinum liquidum (for example with a refractive index (at 20° C.) of from 1.473 to 1.477 and a kinematic viscosity (at 40° C.) of from 30 to 34, and a density (at 20° C.) of from 0.866 to 0.878).

In a particularly preferred embodiment for the purposes of the present invention, the weight ratio of paraffinum liquidum to paraffinum perliquidum is chosen as a:b, where a and b, independently of one another, can be rational numbers from 1 to 5, preferably from 1 to 3. A weight ratio of about 1:1 is particularly preferred.

The texture according to the invention is obtainable particularly if the total amount of one or more mineral oils is chosen from the range from 4 to 10% by weight, in particular from 5 to 7% by weight—in each case based on the total weight of the preparation.

Silicone Oils:

In a particularly preferred embodiment with which the texture according to the invention can be realized particularly well, the oil phase also has a content of cyclic and/or linear silicone oils besides one or more mineral oils.

Advantageously, cyclomethicones, in particular octamethylcyclotetrasiloxane, cyclomethicone D5 and/or cyclomethicone D6 are used as silicone oil to be used according to the invention. A further silicone oil advantageous according to the invention is dimethicone (also: dimethylpolysiloxane or polydimethylsiloxane with the INCI name Dimethicone).

Other silicone oils are, however, also to be used advantageously for the purposes of the present invention, for example hexamethylcyclosiloxane, poly(methylphenylsiloxane), phenyltrimethicone, phenyldimethicone, hexamethylcyclotrisiloxane, polydimethylsiloxane, poly(methylphenylsiloxane), cetyldimethicone, behenyloxydimethicone.

It is, however, also advantageous to choose silicone oils of similar constitution to the compounds referred to above whose organic side chains are derivatized, for example polyethoxylated and/or polypropoxylated. These include, for example, polysiloxane-polyalkyl polyether copolymers, such as cetyl dimethicone copolyol.

For realizing the texture according to the invention, a mixture of cyclic and linear silicone oils, in particular of cyclomethicone and dimethicone, is used particularly advantageously. For the purposes of the present invention, it is particularly preferred in this case to choose the weight ratio of cyclomethicone to dimethicone as a:b, where a and b, independently of one another, may be rational numbers from 1 to 3. A weight ratio of about 1:1 is particularly preferred.

The texture according to the invention is obtainable in particular if the cosmetic preparations comprise, besides one or more mineral oils, also one or more silicone oils (particularly preferably cyclomethicone and dimethicone) in a total amount of from 4 to 10% by weight—based on the total weight of the preparation. It is preferred in this case to choose the weight ratio of all of the mineral oils to all of the silicone oils as a:b, where a and b, independently of one another, may be rational numbers from 1 to 3, preferably 1 to 2. If mineral oil and/or silicone oil mixtures are to be used, the texture according to the invention is then advantageously obtainable if the particular mixtures are formulated as already explained.

Further Oil Phase Constituents:

The oil phase of the preparations according to the invention can also comprise further constituents.

These are advantageously chosen from the group of fatty acid triglycerides, namely the triglycerol esters of saturated and/or unsaturated, branched and/or unbranched alkanecarboxylic acids with a chain length of from 8 to 24, in particular 12 to 18, carbon atoms. For the purposes of the present invention, it is particularly advantageous to use caprylic/capric triglyceride (INCI), particularly if the preparation for the purposes of the present invention also comprises cyclomethicone.

The fatty acid triglycerides can advantageously be chosen from the group of synthetic, semi-synthetic and natural oils, such as, for example, olive oil, sunflower oil, soya oil, peanut oil, rapeseed oil, almond oil, palm oil, coconut oil, castor oil, wheat germ oil, grape seed oil, thistle oil, evening primrose oil and the like.

For the purposes of the present invention, the oil phase can also advantageously comprise substances from the group of esters of saturated and/or unsaturated, branched and/or unbranched alkanecarboxylic acids with a chain length of from 3 to 30 carbon atoms and saturated and/or unsaturated, branched and/or unbranched alcohols with a chain length of from 3 to 30 carbon atoms, and from the group of esters of aromatic carboxylic acids and saturated and/or unsaturated, branched and/or unbranched alcohols with a chain length of from 3 to 30 carbon atoms. Such ester oils can then advantageously be chosen from the group consisting of isopropyl palmitate, isopropyl stearate, n-butyl stearate, n-hexyl laurate, isooctyl stearate, isononyl stearate, isononyl isononanoate, 2-ethylhexyl palmitate, 2-hexyldecyl stearate, 2-octyldodecyl palmitate, erucyl erucate, and synthetic, semi-synthetic and natural mixtures of such esters, such as, for example, jojoba oil.

It is also advantageous to use fat and/or wax components to realize the texture according to the invention. These wax components are advantageously chosen from the group of vegetable waxes, animal waxes, mineral waxes and petrochemical waxes. According to the invention, candelilla wax, carnauba wax, Japan wax, lecithin, wool wax alcohol, wool wax, esparto grass wax, cork wax, guaruma wax, rice germ oil wax, sugar cane wax, berry wax, ouricury wax, montan wax, jojoba wax, shea butter, beeswax, shellac wax, cocoa butter, lanolin (wool wax), uropygial grease, ceresine, ozokerite (earth wax), paraffin waxes and micro waxes, for example, are favourable, provided the conditions required in the main claim are observed.

Further advantageous fat and/or wax components are chemically modified waxes and synthetic waxes, such as, for example, those available under the trade names Synchrowax HRC (glycerol tribehenate), and Synchrowax AW 1C($C_{18-36}$-fatty acid) from Croda GmbH, and also montan ester waxes, sasol waxes, hydrogenated jojoba waxes, synthetic or modified beeswaxes (e.g. dimethicone copolyol beeswax and/or $C_{30-50}$-alkyl beeswax), polyalkylene waxes, polyethylene glycol waxes, but also chemically modified fats, such as, for example, hydrogenated vegetable oils (for example hydrogenated castor oil and/or hydrogenated coconut fatty glycerides), triglycerides, such as, for example, trihydroxystearin, fatty acids, fatty acid esters and glycol esters, such as, for example, $C_{20-40}$-alkyl stearate, $C_{20-40}$-alkylhydroxystearoyl stearate and/or glycol montanate. Further advantageous are also certain organosilicon compounds which have similar physical properties to the specified fat and/or wax components, such as, for example, stearoxytrimethylsilane, provided the conditions required in the main claim are observed. Further fat and/or wax components advantageous according to the invention are those described in EP-1343860-A1, in particular shea butter, which has been enriched with unsaponifiable material (such as, for example, triterpene alcohols).

According to the invention, the fat and/or wax components can be present either individually or in a mixture.

The further constituents of the oil phase may be any mixtures of oil, fat and/or wax components, provided the conditions required in the main claim are observed. It is, for example, advantageous to use Shea butter, particularly if the preparation for the purposes of the present invention also comprises cyclomethicone.

It is advantageous for the purposes of the present invention if the preparations comprise one or more glycerol esters, in particular glycerol esters of α-hydroxycarboxylic acids and saturated fatty acids, where the total amount of the glycerol esters in the finished cosmetic preparations is advantageously chosen from the range from 0.1 to 10.0% by weight, preferably 0.5 to 6.0% by weight, in each case based on the total weight of the preparations.

In addition, it is advantageous for the purposes of the present invention if the preparations comprise one or more fatty alcohols. A preferred fatty alcohol is cetyl alcohol. The total amount of one or more fatty alcohols in the finished cosmetic or dermatological preparations is advantageously chosen from the range from 0.1 to 10.0% by weight, preferably 0.5 to 6.0% by weight, in each case based on the total weight of the preparations.

The aqueous phase of the preparations according to the invention optionally advantageously comprises alcohols, diols or polyols of low carbon number, and also ethers thereof, preferably ethanol, isopropanol, 1,2-propanediol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products.

In addition, for the purposes of the present invention, the preparations can comprise one or more thickeners provided the conditions required in the main claim are observed. The thickener or the thickeners can advantageously be chosen from the group consisting of silicon dioxide, aluminium silicates, polysaccharides and derivatives thereof, e.g. hyaluronic acid, xanthan gum, hydroxypropylmethylcellulose, particularly advantageously from the group of polyacrylates, preferably a polyacrylate from the group of so-called carbopols, for example carbopol grades 980, 981, 1382, 2984, 5984, or else of the grades ETD (easy-to-disperse) 2001, 2020, 2050, in each case individually or in any combinations with one another. It is, however, also advantageous for the purposes of the present invention if the preparations are free from thickeners.

Particularly advantageous preparations are also obtained if antioxidants are used as additives or active ingredients. According to the invention, the preparations advantageously comprise one or more antioxidants. Antioxidants which are favourable, but nevertheless optional, which may be used are all antioxidants which are customary or suitable for cosmetic and/or dermatological applications.

The amount of antioxidants (one or more compounds) in the preparations is preferably 0.001 to 30% by weight, particularly preferably 0.05 to 20% by weight, in particular 1 to 10% by weight, in each case based on the total weight of the preparation.

For the purposes of the present invention, oil-soluble antioxidants can be used particularly advantageously. Preferred antioxidants are vitamin E and derivatives thereof, and vitamin A and derivatives thereof.

If vitamin E and/or derivatives thereof are the antioxidant or the antioxidants, it is advantageous to choose their particular concentrations from the range from 0.001 to 10% by weight, based on the total weight of the formulation.

If vitamin A or vitamin A derivatives, or carotenes or derivatives thereof are the antioxidant or the antioxidants, it is advantageous to choose their particular concentrations from the range from 0.001 to 10% by weight, based on the total weight of the formulation.

It is of course known to the person skilled in the art that cosmetic preparations are mostly inconceivable without the customary auxiliaries and additives. The cosmetic preparations according to the invention can, accordingly, depending on the desired intended use, also comprise cosmetic auxiliaries as are customarily used in such preparations, for example consistency regulators, stabilizers, fillers, preservatives, perfumes, substances for preventing foaming, dyes, pigments which have a colouring effect, surface-active substances, emulsifiers, softening, moisturizing and/or humectant substances, anti-inflammatory substances, additional active ingredients, such as vitamins or proteins, photoprotective agents, insect repellents, bactericides, virucides, water, salt, antimicrobial, proteolytic or keratolytic substances or other customary constituents of a cosmetic formulation, such as alcohols, polyols, polymers, foam stabilizers, organic solvents and also electrolytes.

The latter can, for example, be chosen from the group of salts with the following anions: chlorides, also inorganic oxo element anions. Electrolytes based on organic anions are also advantageous, e.g. lactates, acetates, benzoates, citrates, amino acids, ethylenediaminetetraacetic acid and salts thereof and others besides. As cations of the salts, preference is given to using ammonium, alkali metal, alkaline earth metal, magnesium, iron or zinc ions. It goes without saying that only physiologically acceptable electrolytes should be used in cosmetics. Of particular preference are sodium chloride, magnesium sulphate, magnesium chloride, zinc sulphate and mixtures thereof.

In a particularly preferred embodiment with which the creamy-soft texture according to the invention can be realized particularly well, where the formulations are themselves particularly rich and caring and at the same time ensure a velvety soft feel on the skin following application, the preparations for the purposes of the present invention also comprise one or more active ingredients chosen from the group: ceramide 3, grape seed oil, biotin, panthenol, aloe vera, hamamelis extract, gingko extract, honey, wheat germ oil and almond oil.

The O/W emulsions according to the invention can serve as bases for cosmetic formulations. These can have the customary composition and serve, for example, for the treatment and the care of the skin and/or of the hair, as a lip care product, as deodorant product and as make-up or make-up removal product in decorative cosmetics or as photoprotective preparation. For use, the cosmetic and dermatological preparations according to the invention are applied to the skin and/or the hair in an adequate amount in the manner customary for cosmetics or dermatological products.

Accordingly, cosmetic compositions for the purposes of the present invention can, depending on their formulation, be used, for example, as skin protection cream, cleansing milk, sunscreen lotion, nutrient cream, day or night cream etc. Particular preference for the purposes of the present invention is given to preparations for (large-area) application in the bodycare sector.

For the purposes of the present invention, preparations which are in the form of a sunscreen composition are also favourable. It is, however, also advantageous for the purposes of the present inventions to create preparations whose main purpose is not protection against sunlight, but which nevertheless comprise a content of UV protectants. Thus, for example, UV-A and/or UV-B filter substances are usually incorporated into day creams. For the purposes of the present invention, such preparations preferably comprise at least one UV-A filter substance and/or at least one UV-B filter substance and/or at least one inorganic pigment, especially UV protectants, which, like antioxidants and—if desired—preservatives, represent effective protection of the preparations themselves against decay.

The total amount of filter substances is chosen from the range from 0.1 to 30% by weight, preferably 0.5 to 10% by weight, in particular 1.0 to 6.0% by weight—in each case based on the total weight of the preparations—in order to provide cosmetic preparations which protect the hair and/or the skin from the entire range of ultraviolet radiation.

For the purposes of the present invention, advantageous UV filter substances are:

dibenzoylmethane derivatives, in particular 4-(tert-butyl)-4'-methoxydibenzoylmethane (CAS No. 70356-09-1), which is sold by Givaudan under the brand Parsol® 1789 and by Merck under the trade name Eusolex® 9020.

phenylene-1,4-bis(2-benzimidazole)-3,3'-5,5'-tetrasulphonic acid and its salts, particularly the corresponding sodium, potassium or triethanolammonium salts, in particular the phenylene-1,4-bis(2-benzimidazole)-3,3'-5,5'-tetrasulphonic acid bis-sodium salt with the INCI name Disodium Phenyl Dibenzimidazole Tetrasulphonate (CAS No.: 180898-37-7), which is available, for example, under the trade name Neo Heliopan AP from Symrise;

salts of 2-phenylbenzimidazole-5-sulphonic acid, such as its sodium, potassium or its triethanolammonium salt, and the sulphonic acid itself with the INCI name phenylbenzimidazolesulphonic acid (CAS No.: 27503-81-7), which is available, for example, under the trade name Eusolex 232 from Merck or under Neo Heliopan Hydro from Symrise;

1,4-di(2-oxo-10-sulpho-3-bornylidenemethyl)benzene (also: –3,3'-(1,4-phenylenedimethylene)bis(7,7-dimethyl-2-oxobicyclo[2.2.1]hept-1-ylmethanesulphonic acid) and salts thereof (particularly the corresponding 10-sulphato compounds, in particular the corresponding sodium, potassium or triethanolammonium salt), which is also referred to as benzene-1,4-di(2-oxo-3-bornylidenemethyl-10-sulphonic acid). Benzene-1,4-di(2-oxo-3-bornylidenemethyl-10-sulphonic acid) has the INCI name terephthalidene dicamphor sulphonic acid (CAS No.: 90457-82-2) and is obtainable, for example, under the trade name Mexoryl SX from Chimex;

sulphonic acid derivatives of 3-benzylidenecamphor, such as, for example, 4-(2-oxo-3-bornylidenemethyl)benzenesulphonic acid, 2-methyl-5-(2-oxo-3-bornylidenemethyl)sulphonic acid and salts thereof.

benzoxazole derivatives, such as, for example, 2,4-bis[5,1-(dimethylpropyl)benzoxazol-2-yl(4-phenyl)imino]-6-(2-ethylhexyl)imino-1,3,5-triazine with the CAS No. 288254-16-0, which is obtainable from 3V sigma under the trade name Uvasorb® K2A.

hydroxybenzophenones, e.g. hexyl 2-(4'-diethylamino-2'-hydroxybenzoyl)benzoate (also: aminobenzophenone), which is obtainable under the trade name Uvinul A Plus from BASF.

triazine derivatives, such as, for example, 2,4-bis{[4-(2-ethylhexyloxy)-2-hydroxy]phenyl}-6-(4-methoxyphenyl)-1-1,3,5-triazine (INCI=bis-ethylhexyl-oxyphenol methylphenyl triazine), which is obtainable under the trade name Tinosorb® S from Ciba-Chemikalien GmbH; dioctylbutylamidotriazone (INCI: diethylhexyl butamido triazone), which is obtainable under the trade name UVASORB HEB from Sigma 3V; tris(2-ethylhexyl) 4,4',4"-(1,3,5-triazine-2,4,6-triyltriimino)trisbenzoate, also: 2,4,6-tris[anilino(p-carbo-2'-ethyl-1'-hexyloxy)]-1,3,5-triazine (INCI: ethylhexyl triazone), which is sold by BASF Aktiengesellschaft under the trade name Uvinul® T 150; 2-[4,6-bis(2,4-dimethylphenyl)-1,3,5-triazin-2-yl]-5-(octyloxy)phenol (CAS No.: 2725-22-6).

benzotriazoles, such as, for example, 2,2'-methylenebis(6-(2H-benzotriazol-2-yl)-4-(1,1,3,3-tetramethylbutyl)phenol) (INCI: methylene bisbenzotriazolyl tetra-methylbutylphenol), which is obtainable, for example, under the trade name Tinosorb® M from Ciba Chemikalien GmbH.

3-benzylidenecamphor derivatives, preferably 3-(4-methylbenzylidene)camphor, 3-benzylidenecamphor;

4-aminobenzoic acid derivatives, preferably 2-ethylhexyl 4-(dimethylamino)benzoate, amyl 4-(dimethylamino)benzoate;

esters of benzylmalonic acid, preferably di(2-ethylhexyl) 4-methoxybenzylmalonate;

esters of cinnamic acid, preferably 2-ethylhexyl 4-methoxycinnamate, isopentyl 4-methoxycinnamate;

derivatives of benzophenone, preferably 2-hydroxy-4-methoxybenzophenone, 2-hydroxy-4-methoxy-4'-methylbenzophenone, 2,2'-dihydroxy-4-methoxybenzophenone, and UV filters bonded to polymers ethylhexyl 2-cyano-3,3-diphenylacrylate (octocrylene), which is obtainable from BASF under the name Uvinul® N539T.

Preparations according to the invention can also comprise inorganic pigments which are customarily used in cosmetics for protecting the skin against UV rays. These are oxides of titanium, zinc, iron, zirconium, silicon, manganese, aluminium, cerium and mixtures thereof, and also modifications in which the oxides are the active agents. They are particularly preferably pigments based on titanium dioxide.

For the purposes of the present invention, the pigments may also be used in the form of commercially obtainable oily or aqueous predispersions. Dispersion auxiliaries and/or solubilization promoters may advantageously be added to these predispersions.

According to the invention, the pigments can advantageously be surface-treated ("coated"), the intention being, for example, to form and/or retain a hydrophilic, amphiphillic or hydrophobic character. This surface treatment can consist in providing the pigments with a thin hydrophilic and/or hydrophobic inorganic and/or organic layer by methods known per se. For the purposes of the present invention, the various surface coatings can also comprise water.

An advantageous organic pigment for the purposes of the present invention is 2,2'-methylenebis(6-(2H-benzotriazol-2-yl)-4-(1,1,3,3-tetramethylbutyl)phenol) [INCI: Bisoctyltriazole], which is obtainable under the trade name Tinosorb® M from Ciba-Chemikalien GmbH.

The examples below are intended to illustrate the present invention without limiting it. The numerical values in the examples are percentages by weight, based on the total weight of the particular preparations.

O/W Emulsions

| Formulation Example Nos. | 1 | 2 | 3 | 4 | 5 |
|---|---|---|---|---|---|
| Glyceryl stearate | 1.0 | 2.0 | 2.0 | 0.5 | 0.25 |
| Polyethylene glycol (40) stearate | 1.0 | 1.0 | 1.0 | — | — |
| Cyclomethicone | 2.5 | 2.9 | 2.9 | 5.0 | 7.5 |
| Dimethicone | 5.0 | 2.8 | 2.8 | 2.0 | 5.0 |
| Behenyl alcohol | 1.5 | — | — | 1 | — |
| Stearyl alcohol | — | — | — | 1 | — |
| Cetyl alcohol | — | 3.0 | 3.0 | 1 | — |
| Tocopherol acetate | 0.5 | — | 0.5 | — | — |
| Shea butter | 1.5 | — | 0.5 | 0.75 | 2.5 |
| Mineral oil, medicinal quality, low viscosity | 4.5 | 3.0 | 3.0 | — | 0.25 |
| Mineral oil, medicinal quality, higher viscosity | — | 3.0 | 3.0 | 2.0 | 0.25 |
| Caprylic/capric triglyceride | 0.7 | 3.1 | 3.1 | 3.0 | 0.25 |
| Perfume | q.s. | q.s. | q.s. | q.s. | q.s. |
| Methylparaben | — | 0.2 | 0.3 | 0.3 | 0.4 |
| Propylparaben | 0.06 | 0.1 | 0.1 | 0.15 | — |
| Methyl-, propyl-, ethyl-, butyl-, isobutylparaben + phenoxyethanol | 0.6 | — | — | — | 0.1 |
| Phenoxyethanol | — | 0.5 | 0.5 | — | — |
| Gingko extract | 0.4 | — | 0.5 | — | — |
| EDTA, sodium salt | 0.1 | — | 0.2 | — | — |
| Glycerol | 5 | 10 | 10 | 15 | 7.5 |
| Polyacrylic acid, sodium salt | 0.02 | 0.02 | 0.02 | 0.15 | 0.04 |
| Ceramide 3 | 0.01 | 0.01 | — | — | — |
| Grape seed oil | 2.0 | 0.2 | — | — | — |
| Ethanol | 2.0 | — | — | 5.0 | 1.0 |
| Biotin | 0.004 | 0.004 | — | — | — |
| Modified starch | 0.5 | — | — | 0.15 | — |
| Water | ad 100 | ad 100 | ad 100 | ad 100 | ad 100 |

O/W Emulsions

| Formulation Example Nos. | 6 | 7 | 8 | 9 | 10 |
|---|---|---|---|---|---|
| Polyethylene glycol (21) stearyl ether | 1 | — | 2.5 | 2 | 1.5 |
| Polyethylene glycol (2) stearyl ether | 1 | — | 5.5 | 3 | 7.5 |
| Glyceryl stearate, self-emulsifying | — | 8 | — | — | — |
| Behenyl alcohol | 3 | 2 | — | 1 | — |
| Stearyl alcohol | 3 | 2 | — | 2 | — |
| Cetylstearyl alcohol | 3 | 4 | — | — | 2 |
| Hydrogenated poly-isobutene | 0.5 | 0.75 | 1.0 | 2.0 | 0.25 |
| Octyldodecanol | 0.5 | 1.0 | 0.75 | 3.0 | 0.25 |
| Glycerol | 5 | 10 | 15 | 3 | 7.5 |
| Shea butter | 1.5 | — | 0.5 | — | 2.5 |
| Perfume | q.s. | q.s. | q.s. | q.s. | q.s. |
| Mineral oil, medicinal quality, low viscosity | 4.5 | 3.0 | 3.0 | — | 0.25 |
| Mineral oil, medicinal quality, higher viscosity | — | 3.0 | 3.0 | 2.0 | 0.25 |
| Methylparaben | 0.4 | 0.1 | 0.05 | 0.3 | 0.4 |
| Propylparaben | 0.3 | 0.4 | 0.25 | 0.15 | — |
| Iodopropynyl butylcarbamate | — | — | 0.05 | — | 0.1 |
| Modified starch | 0.5 | — | — | 0.15 | — |
| Water | ad 100 | ad 100 | ad 100 | ad 100 | ad 100 |

COMPARATIVE EXAMPLES

The preparations SOFTMI 60 (according to the invention) and DIV 192 (comparative example) were prepared in the usual way from constituents listed below. The flow curves were ascertained for these and also for the two commercial products "CLINIQUE® ALOE BODY BALM" and "HELENA RUBINSTEIN® BODY HYDRATOR" (full INCI declaration likewise given below).

The flow curves are shown in FIG. 1.

As can clearly been seen, only the preparation SOFTMI 60 has the properties according to the invention—a maximum of 2250 Pa·s in the range from 5 to 15 Pa and also in the further course of the flow curve at a shear stress of about 40 to about 70 Pa, a shoulder. These rheological flow properties help to characterize the creamy-soft texture ("good-feel texture") for the purposes of the present invention.

| SOFTMI 60 | % by wt. |
|---|---|
| Caprylic/capric triglyceride | 3.1000 |
| Carbomer | 0.0200 |
| Cetyl alcohol | 3.0000 |
| Cyclomethicone | 2.9000 |
| Dimethicone | 2.8000 |
| Perfume | q.s. |
| Glycerol | 10.0000 |
| Glyceryl stearate | 2.0000 |
| Methylparaben | 0.3000 |
| Mineral oil, medicinal quality, low viscosity | 3.0000 |
| Mineral oil, medicinal quality, higher viscosity | 3.0000 |
| PG-40 stearate | 1.0000 |
| Phenoxyethanol | 0.5000 |
| Propylparaben | 0.1000 |
| Water | ad 100 |

| DIV 192 | % by wt. |
|---|---|
| Aluminium starch octenylsuccinate (INCI name) | 1.0000 |
| Cyclomethicone | 3.0000 |
| Dicaprylyl ether | 3.0000 |
| Dimethicone | 2.0000 |
| Glycerol | 10.0000 |
| Glyceryl stearate | 4.0000 |
| Lactic acid | 0.3500 |
| Methylparaben | 0.3000 |
| PEG-40 stearate | 2.0000 |
| Phenoxyethanol | 0.5000 |
| Propylparaben | 0.1000 |
| Sodium lactate | 5.0000 |
| Stearyl alcohol | 4.0000 |
| Urea | 5.0000 |
| Xanthan gum | 0.1000 |
| Water | ad 100 |

CLINIQUE® ALOE BODY BALM:

Water, Aloe Barbadensis, Butylene Glycol, Squalane, Caprylic/Capric Stearic Triglyceride, C10-30 Cholesterol/Lanosterol Esters, Octyl Methoxycinnamate, PEG-40 Stearate, Cetyl Acetate, Glyceryl Stearate, Anthemis Nobilis, Carbomer, Acetylated Lanolin Alcohol, Trometamine, Trisodium EDTA, Imidazolidinyl Urea, Methylparaben, Propylparaben, Butylparaben, Cl 19140, Cl 42090.

HELENA RUBINSTEIN® BODY HYDRATOR:

Water, Octyl Palmitate, Glycerin, Paraffinum Liquidum, Dimethicone, Propylene Glycol, Octyl Dimethyl Paba, PEG-40 Stearate, Hydrolyzed Wheat Protein, Inulin, Carbomer, Hydroxyethylcellulose, Glyceryl Polyacrylate, Cetyl Alcohol, Sorbitan Tristearate, Triethanolamine, Parfum, Disodium EDTA, Imidazolidinyl Urea, Methylparaben, Phenoxyethanol, Propylparaben.

That which is claimed:

1. A cosmetic preparation, wherein the preparation is of the oil-in-water type and comprises an oil phase comprising mineral oils selected from paraffinum liquidum and paraffinum perliquidum in a total amount of from 4% to 10% by weight, based on a total weight of the preparation, a weight ratio of paraffinum liquidum to paraffinum perliquidum being from 1:3 to 3:1, and wherein the preparation has a flow curve which depicts the dynamic viscosity as a function of the shear stress and shows:
   a. a maximum of up to 10 000 Pas at a shear stress from 5 to 50 Pa; and
   b. a shoulder at a shear stress of from 30 to 110 Pa, the flow curve recorded using an SR-2000 from Rheometric Scientific, the measurement system comprising a parallel plate measuring system with a diameter of 25 mm, the measurement being carried out at a measuring temperature of 25° C., and the measurement method comprising a linear shear stress-time slope with a strain rate of 40 Pa/min starting at 0 Pa.

2. The preparation of claim 1, wherein a totality of the mineral oils in the oil phase has:
   a refractive index at 20° C. of from 1.475 to 1.480,
   a kinematic viscosity at 40° C. of from 35 to 65 $mm^2$/s, and
   a density at 20° C. of from 0.870 to 0.880 $g/cm^3$.

3. The preparation of claim 1, wherein the total amount of the mineral oils is from 5% to 7% by weight.

4. The preparation of claim 1, wherein a weight ratio of paraffinum liquidum to paraffinum perliquidum is about 1:1.

5. The preparation of claim 1, wherein the preparation further comprises one or more silicone oils selected from cyclic silicone oils and linear silicone oils.

6. The preparation of claim 5, wherein the preparation comprises a mixture of one or more cyclic silicone oils and one or more linear silicone oils.

7. The preparation of claim 6, wherein the one or more cyclic silicone oils comprise cyclomethicone and the one or more linear silicone oils comprise dimethicone.

8. The preparation of claim 7, wherein a weight ratio of cyclomethicone to dimethicone is about 1:1.

9. The preparation of claim 5, wherein a total amount of the one or more silicone oils is from 4% to 10% by weight, based on a total weight of the preparation.

10. The preparation of claim 5, wherein a weight ratio of the mineral oils to the one or more silicone oils is from 1:3 to 3:1.

11. The preparation of claim 10, wherein the weight ratio is from 1:2 to 2:1.

12. The preparation of claim 1, wherein the oil phase further comprises one or more substances selected from fats and waxes.

13. The preparation of claim 12, wherein the fats and waxes are selected from one or more of candelilla wax, carnauba wax, Japan wax, lecithin, wool wax alcohol, wool wax, esparto grass wax, cork wax, guaruma wax, rice germ oil wax, sugar cane wax, berry wax, ouricury wax, montan wax, jojoba wax, shea butter, beeswax, shellac wax, cocoa butter, lanolin, uropygial grease, ceresine, ozokerite, paraffin waxes, and micro waxes.

14. The preparation of claim 12, wherein the oil phase comprises shea butter.

15. The preparation of claim 14, wherein the preparation further comprises cyclomethicone.

16. The preparation of claim 1, wherein the preparation further comprises one or more active ingredients selected from ceramide 3, grape seed oil, biotin, panthenol, aloe vera, hamamelis extract, gingko extract, honey, wheat germ oil, and almond oil.

17. A cosmetic preparation, wherein the preparation is of the oil-in-water type and comprises an oil phase comprising mineral oils selected from paraffinum liquidum and paraffinum perliquidum in a total amount of from 5% to 7% by weight, based on a total weight of the preparation, a weight ratio of paraffinum liquidum to paraffinum perliquidum being from 1:3 to 3:1, and wherein the preparation has a flow curve which depicts the dynamic viscosity as a function of the shear stress and shows:
   a, a maximum of up to 10 000 Pas at a shear stress from 5 to 50 Pa; and
   b, a shoulder at a shear stress of from 30 to 110 Pa, the flow curve recorded using an SR-2000 from Rheometric Scientific, the measurement system comprising a parallel plate measuring system with a diameter of 25 mm, the measurement being carried out at a measuring temperature of 25° C., and the measurement method comprising a linear shear stress-time slope with a strain rate of 40 Pa/min starting at 0 Pa.

18. The preparation of claim 17, wherein a totality of the mineral oils in the oil phase has:
   a refractive index at 20° C. of from 1.475 to 1.480,
   a kinematic viscosity at 40° C. of from 35 to 65 $mm^2$/s, and
   a density at 20° C. of from 0.870 to 0.880 $g/cm^3$.

19. The preparation of claim 17, wherein the preparation further comprises from 4% to 10% by weight, based on a total weight of the preparation, of one or more silicone oils selected from cyclic silicone oils and linear silicone oils.

20. The preparation of claim 19, wherein the one or more silicone oils comprise a mixture of one or more cyclic silicone oils and one or more linear silicone oils.

21. The preparation of claim 20, wherein the one or more cyclic silicone oils comprise cyclomethicone and the one or more linear silicone oils comprise dimethicone.

22. The preparation of claim 21, wherein a weight ratio of cyclomethicone to dimethicone is about 1:1.

23. The preparation of claim 20, wherein a weight ratio of the mineral oils to the one or more silicone oils is from 1:3 to 3:1.

24. The preparation of claim 23, wherein the weight ratio is from 1:2 to 2:1.

25. The preparation of claim 18, wherein the preparation further comprises one or more silicone oils selected from cyclic silicone oils and linear silicone oils.

26. The preparation of claim 25, wherein a weight ratio of the mineral oils to the one or more silicone oils is from 1:3 to 3:1.

* * * * *